United States Patent
Ito (10) Patent No.: US 11,730,384 B2
(45) Date of Patent: Aug. 22, 2023

(54) FLUID ANALYSIS APPARATUS, METHOD FOR OPERATING FLUID ANALYSIS APPARATUS, AND FLUID ANALYSIS PROGRAM

(71) Applicant: FUJIFILM Corporation, Tokyo (JP)

(72) Inventor: Hirotaka Ito, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 135 days.

(21) Appl. No.: 16/782,081

(22) Filed: Feb. 5, 2020

(65) Prior Publication Data
US 2020/0170519 A1 Jun. 4, 2020

Related U.S. Application Data

(63) Continuation of application No. PCT/JP2018/022324, filed on Jun. 12, 2018.

(30) Foreign Application Priority Data

Sep. 19, 2017 (JP) ................. 2017-179168

(51) Int. Cl.
*A61B 5/026* (2006.01)
*A61B 5/00* (2006.01)
(Continued)

(52) U.S. Cl.
CPC .......... *A61B 5/0263* (2013.01); *A61B 5/0042* (2013.01); *G01R 33/5601* (2013.01);
(Continued)

(58) Field of Classification Search
CPC ..... A61B 5/0263; A61B 5/0042; A61B 6/507; A61B 8/06; G01R 33/5601; G01R 33/56325
See application file for complete search history.

(56) References Cited

U.S. PATENT DOCUMENTS

2009/0143667 A1 6/2009 Kovacs et al.
2010/0094122 A1 4/2010 Kiraly
(Continued)

FOREIGN PATENT DOCUMENTS

JP H02143167 6/1990
JP H0549640 3/1993
(Continued)

OTHER PUBLICATIONS

Pereira, V.M., et al. "A DSA-Based Method Using Contrast-Motion Estimation for the Assessment of the Intra-Aneurysmal Flow Changes Induced by Flow-Diverter Stents," American Journal of Neuroradiology. vol. 34, 2013. p. 808-815 (Year: 2013).*
(Continued)

*Primary Examiner* — Keith M Raymond
*Assistant Examiner* — Sean A Frith
(74) *Attorney, Agent, or Firm* — JCIPRNET (57) ABSTRACT

The invention provides a fluid analysis apparatus, a method for operating a fluid analysis apparatus, and a fluid analysis program that display a flow velocity vector such that the tendency of a fluid flow is easily checked. A representative two-dimensional flow velocity vector representing a plurality of two-dimensional flow velocity vectors obtained by projecting three-dimensional flow velocity vectors of a plurality of voxels that overlap each other in a projection direction of a projection plane to the projection plane is acquired from three-dimensional volume data that has information of the three-dimensional flow velocity vector indicating the flow velocity of a fluid in an anatomical structure for each voxel and is displayed.

16 Claims, 8 Drawing Sheets

(51) Int. Cl.
    *G01R 33/56*     (2006.01)
    *G01R 33/563*     (2006.01)
    *A61B 6/00*     (2006.01)
    *A61B 8/06*     (2006.01)

(52) U.S. Cl.
    CPC ........ *G01R 33/56325* (2013.01); *A61B 6/507* (2013.01); *A61B 8/06* (2013.01)

(56) References Cited

U.S. PATENT DOCUMENTS

| | | | |
|---|---|---|---|
| 2011/0077526 A1* | 3/2011 | Zwirn | A61B 5/6805 600/459 |
| 2011/0175608 A1* | 7/2011 | McNeal | G01R 33/56316 324/306 |
| 2011/0196237 A1* | 8/2011 | Pelissier | A61B 8/543 600/454 |
| 2014/0276072 A1* | 9/2014 | Martins | A61B 8/463 600/454 |
| 2014/0316758 A1 | 10/2014 | Yagi et al. | |
| 2015/0032435 A1* | 1/2015 | Yagi | A61B 5/055 703/11 |
| 2016/0015366 A1* | 1/2016 | Haugaard | A61B 8/5223 600/447 |
| 2016/0220123 A1* | 8/2016 | Grady | A61B 5/7278 |
| 2016/0232660 A1 | 8/2016 | Bannae et al. | |
| 2016/0361040 A1* | 12/2016 | Tanaka | A61B 8/14 |

FOREIGN PATENT DOCUMENTS

| | | | | |
|---|---|---|---|---|
| JP | 2002191600 | | 7/2002 | |
| JP | 2002191600 A | * | 7/2002 | ......... G01S 15/8993 |
| JP | 2007135894 | | 6/2007 | |
| JP | 2009279290 | | 12/2009 | |
| JP | 2009279290 A | * | 12/2009 | |
| JP | 2012045253 | | 3/2012 | |
| JP | 2016140683 | | 8/2016 | |
| JP | 2017051424 | | 3/2017 | |
| WO | 2013031741 | | 3/2013 | |
| WO | 2014185521 | | 11/2014 | |
| WO | WO-2014185521 A1 | * | 11/2014 | ........... A61B 5/0044 |

OTHER PUBLICATIONS

"International Search Report (Form PCT/ISA/210) of PCT/JP2018/022324," dated Aug. 28, 2018, with English translation thereof, pp. 1-5.

"Written Opinion of the International Searching Authority (Form PCT/ISA/237) of PCT/JP2018/022324," dated Aug. 28, 2018, with English translation thereof, pp. 1-9.

Ian Marshall, et al., "MRI and CFD studies of pulsatile flow in healthy and stenosed carotid bifurcation models," Journal of Biomechanics, vol. 37, May 2004, pp. 1-10.

"Office Action of Japan Counterpart Application", dated Feb. 24, 2021, with English translation thereof, p. 1-p. 5.

* cited by examiner

FLUID ANALYSIS APPARATUS, METHOD FOR OPERATING FLUID ANALYSIS APPARATUS, AND FLUID ANALYSIS PROGRAM

CROSS-REFERENCE TO RELATED APPLICATIONS

This application is a Continuation of PCT International Application No. PCT/JP2018/022324 filed on Jun. 12, 2018, which claims priority under 35 U.S.C. § 119(a) to Japanese Patent Application No. 2017-179168 filed on Sep. 19, 2017. Each of the above application(s) is hereby expressly incorporated by reference, in its entirety, into the present application.

BACKGROUND OF THE INVENTION

1. Field of the Invention

The present invention relates to a fluid analysis apparatus, a method for operating a fluid analysis apparatus, and a fluid analysis program that display a flow velocity of a fluid in an anatomical structure.

2. Description of the Related Art

In recent years, for example, many studies have been reported which use a blood flow for diagnosis or treatment. For example, a method has been used which checks a blood flow with simulation using a 4D flow technique that four-dimensionally measures the actual blood flow or blood flow analysis using computational fluid dynamics (CFD).

In a case in which the blood flow analysis method using a medical image is used, for example, it is possible to display a flow velocity vector for each voxel, each pixel, or each region on a three-dimensional plane or a two-dimensional plane, using an ultrasound image or a magnetic resonance imaging (MRI) image captured by a three-dimensional cine phase contrast magnetic resonance method. In addition, a method has been proposed which generates a blood vessel model from a CT image or an MM image captured by administering a contrast agent and performs CFD on the basis of the blood vessel model to calculate a flow velocity vector.

In a case in which a heart disease of a patient is diagnosed, it is desirable that the flow velocity of blood can be displayed as a vector and can be checked. In the initial stage of image diagnosis, at the time of conferences or conference presentations, or at the time of patient explanations, it is useful to simply display the entire image of a blood flow in an easy-to-understand manner. Various display methods have been examined.

JP1990-143167 (JP-H02-143167A) discloses a method which projects a three-dimensional flow velocity vector onto a plane and displays a two-dimensional flow velocity vector. JP1993-049640 (JP-H05-049640A) discloses a method which calculates a predetermined range of each component of fluid velocity vectors from an average value, converts data of a fluid velocity vector that does not fall within the range into a zero vector, and suppresses the display of a fluid velocity vector having a variation in size or orientation compared to the average fluid velocity vector in an ultrasound diagnostic apparatus that calculates and displays a fluid velocity vector. JP2017-051424A discloses a method which calculates a two-dimensional blood flow vector related to the velocity of a fluid at each position in a predetermined cross section, using a three-dimensional motion vector indicating the motion of the heart and Doppler information, in order to obtain a flow velocity vector close to the actual blood flow in consideration of the original three-dimensional motion of the heart.

SUMMARY OF THE INVENTION

Figure 14:
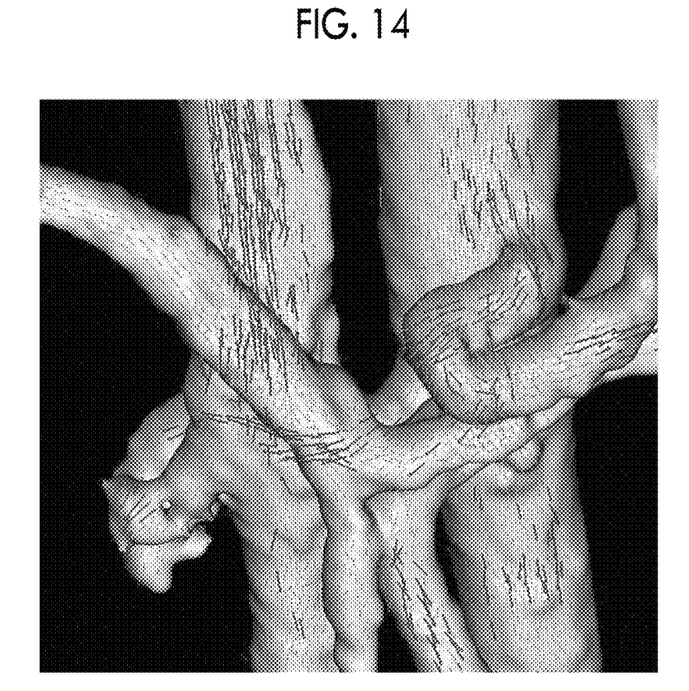
FIG. 14 illustrates an example of the display of a flow velocity vector according to the related art.

In the related art, as illustrated in FIG. 14, a method is widely used which displays a velocity vector of each voxel on a three-dimensional projection image. However, since there are many vectors and the vectors overlap each other in display, it is difficult to distinguish the relationship between the front and the back. Therefore, it is difficult to quickly and intuitively check the tendency of a three-dimensional flow.

Accordingly, in order to solve the above-mentioned problems, an object of the invention is to provide a fluid analysis apparatus, a method for operating a fluid analysis apparatus, and a fluid analysis program that display a flow velocity vector such that the tendency of a fluid flow is easily checked.

According to the invention, there is provided a fluid analysis apparatus comprising: a vector acquisition unit that acquires, from three-dimensional volume data obtained by capturing an image of an object including an anatomical structure in which a fluid flows, information of a three-dimensional flow velocity vector indicating a flow velocity of the fluid in the anatomical structure for each voxel, and acquires, from a plurality of two-dimensional flow velocity vectors obtained by projecting three-dimensional flow velocity vectors of a plurality of voxels overlapping in a projection direction of a projection plane to the projection plane, a representative two-dimensional flow velocity vector representing the plurality of two-dimensional flow velocity vectors; and a display unit that displays the representative two-dimensional flow velocity vector projected to the projection plane.

According to the invention, there is provided a method for operating a fluid analysis apparatus comprising a vector acquisition unit and a display unit. The method comprises: allowing the vector acquisition unit to acquire, from three-dimensional volume data obtained by capturing an image of an object including an anatomical structure in which a fluid flows, information of a three-dimensional flow velocity vector indicating a flow velocity of the fluid in the anatomical structure for each voxel, and to acquire, from a plurality of two-dimensional flow velocity vectors obtained by projecting three-dimensional flow velocity vectors of a plurality of voxels overlapping in a projection direction of a projection plane to the projection plane, a representative two-dimensional flow velocity vector representing the plurality of two-dimensional flow velocity vectors; and allowing the display unit to display the representative two-dimensional flow velocity vector projected to the projection plane.

According to the invention, there is provided a fluid analysis program that causes a computer to function as: a vector acquisition unit that acquires, from three-dimensional volume data obtained by capturing an image of an object including an anatomical structure in which a fluid flows, information of a three-dimensional flow velocity vector indicating a flow velocity of the fluid in the anatomical structure for each voxel, and acquires, from a plurality of two-dimensional flow velocity vectors obtained by projecting three-dimensional flow velocity vectors of a plurality of voxels overlapping in a projection direction of a projection plane to the projection plane, a representative two-dimensional flow velocity vector representing the plurality of two-dimensional flow velocity vectors; and a display unit that displays the representative two-dimensional flow velocity vector projected to the projection plane.

The "anatomical structure" means a structure forming a body such as a tissue or an organ.

In addition, the "three-dimensional volume data" is formed by voxels obtained by finely dividing a three-dimensional space and includes data indicating the flow velocity of a fluid existing at the position of each voxel or physical quantities corresponding to the amount of transmission of radiation or magnetism through organs or tissues. For example, specifically, each voxel has data, such as the value of the flow velocity of a fluid, such as blood, and a concentration value corresponding to an organ or a tissue. The concentration value also includes a concentration value of a fluid, such as blood, included in a tissue, such as a blood vessel. Further, the "three-dimensional flow velocity vector" may be acquired from the value of the flow velocity of each voxel or may be acquired from the amount of movement of the concentration value corresponding to the tissue.

The anatomical structures may at least partially overlap each other in the projection direction and the representative two-dimensional flow velocity vector may be a two-dimensional flow velocity vector representing two-dimensional flow velocity vectors obtained by projecting three-dimensional flow velocity vectors in an anatomical structure close to the projection plane among the overlapped anatomical structures.

The representative two-dimensional flow velocity vector may be a two-dimensional flow velocity vector obtained by projecting a three-dimensional flow velocity vector with a maximum size among the three-dimensional flow velocity vectors that overlap each other in the projection direction or an average three-dimensional flow velocity vector obtained by averaging the three-dimensional flow velocity vectors that overlap each other in the projection direction.

The representative two-dimensional flow velocity vector may be a two-dimensional flow velocity vector with a maximum size among two-dimensional flow velocity vectors obtained by projecting the three-dimensional flow velocity vectors that overlap each other in the projection direction or an average two-dimensional flow velocity vector obtained by averaging the two-dimensional flow velocity vectors obtained by projecting the three-dimensional flow velocity vectors that overlap each other in the projection direction.

The representative two-dimensional flow velocity vector may be a two-dimensional flow velocity vector obtained by projecting a three-dimensional flow velocity vector with a maximum size among the three-dimensional flow velocity vectors that overlap each other in the projection direction or an average three-dimensional flow velocity vector obtained by averaging the three-dimensional flow velocity vectors that overlap each other in the projection direction in the anatomical structure close to the projection plane among the overlapped anatomical structures.

The representative two-dimensional flow velocity vector may be a two-dimensional flow velocity vector with a maximum size among two-dimensional flow velocity vectors obtained by projecting the three-dimensional flow velocity vectors that overlap each other in the projection direction or an average two-dimensional flow velocity vector obtained by averaging the two-dimensional flow velocity vectors obtained by projecting the three-dimensional flow velocity vectors that overlap each other in the projection direction in the anatomical structure close to the projection plane among the overlapped anatomical structures.

The three-dimensional flow velocity vector may be acquired from three-dimensional volume data captured by a three-dimensional cine phase contrast magnetic resonance method.

The display unit may display the representative two-dimensional flow velocity vector so as to be superimposed on a morphological image of the anatomical structure.

Further, the "morphology" means the appearance of a tissue or an organ as viewed from the outside and the "morphology of the anatomical structure" means the appearance of the anatomical structure as viewed from the outside. For example, specifically, in a case in which the anatomical structure is a blood vessel, the "morphology of the anatomical structure" indicates the appearance of the blood vessel as viewed from the outside and the morphological image can be generated by, for example, volume rendering.

The anatomical structure may be a blood vessel, the fluid may be blood, and the three-dimensional flow velocity vector may be a flow velocity vector of the blood.

The three-dimensional flow velocity vector may be obtained by a result of blood flow analysis using computational fluid dynamics.

The fluid may be cerebrospinal fluid and the three-dimensional flow velocity vector may be a flow velocity vector of the cerebrospinal fluid.

Another fluid analysis apparatus according to the invention comprises a memory that stores commands to be executed by a computer and a processor that is configured to execute the stored commands. The processor performs a process of acquiring, from three-dimensional volume data that is obtained by capturing an image of an object including an anatomical structure in which a fluid flows and has information of a three-dimensional flow velocity vector indicating a flow velocity of the fluid in the anatomical structure for each voxel, a representative two-dimensional flow velocity vector representing a plurality of two-dimensional flow velocity vectors among the plurality of two-dimensional flow velocity vectors obtained by projecting three-dimensional flow velocity vectors of a plurality of voxels overlapping in a projection direction of a projection plane to the projection plane and a process of displaying the representative two-dimensional flow velocity vector projected to the projection plane.

According to the invention, the representative two-dimensional flow velocity vector representing a plurality of two-dimensional flow velocity vectors obtained by projecting the three-dimensional flow velocity vectors of a plurality of voxels overlapping in the projection direction of the projection plane to the projection plane among the plurality of two-dimensional flow velocity vectors is acquired from the three-dimensional volume data that has the information of the three-dimensional flow velocity vector indicating the flow velocity of the fluid in the anatomical structure for each voxel and is displayed. Therefore, it is possible to quickly and intuitively check the tendency of a three-dimensional flow.

DESCRIPTION OF THE PREFERRED EMBODIMENTS

Figure 1:
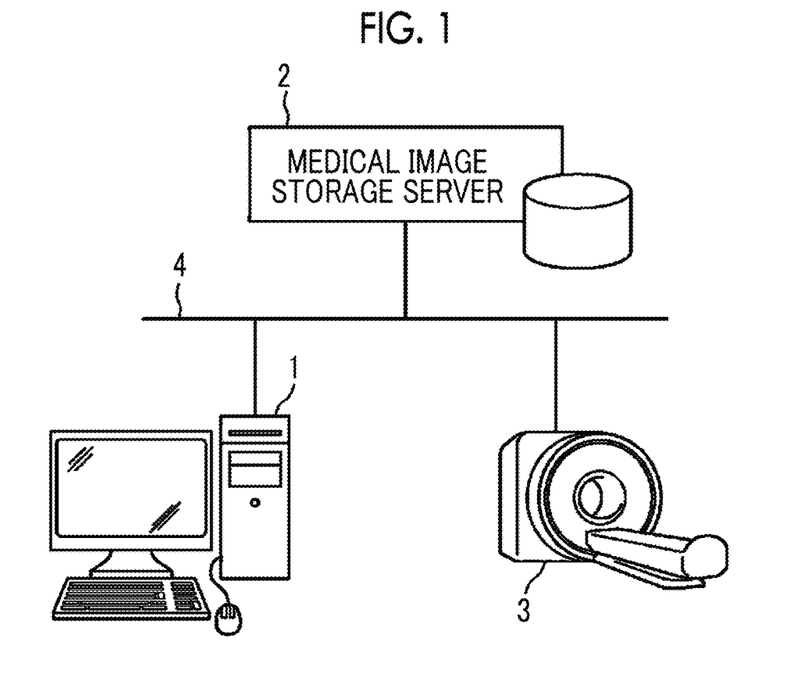
FIG. 1 is a diagram schematically illustrating the configuration of a medical information system.

Hereinafter, a medical information system comprising a fluid analysis apparatus according to a first embodiment of the invention will be described with reference to the drawings. FIG. 1 is a block diagram schematically illustrating the configuration of the medical information system according to this embodiment.

Specifically, as illustrated in FIG. 1, the medical information system according to this embodiment is configured by connecting a fluid analysis apparatus 1, a medical image storage server 2, and an imaging apparatus 3 (hereinafter, referred to as a modality) through a network 4 so as to communicate with each other.

The modality 3 is, for example, a computed tomography (CT) apparatus, a magnetic resonance imaging (MRI) apparatus, or an ultrasonography apparatus. Captured three-dimensional volume data is transmitted to the medical image storage server 2 through the network 4 according to a storage format based on a digital imaging and communication in medicine (DICOM) standard and a communication standard and is then stored therein.

The fluid analysis apparatus 1 is a general-purpose computer and comprises known hardware configurations, such as a central processing unit (CPU), a memory (main storage device), a storage (auxiliary storage device), an input/output interface, a communication interface, an input device, a display device, and a data bus. For example, a known operation system is installed in the fluid analysis apparatus 1. In addition, for example, the fluid analysis apparatus 1 has a liquid crystal display as the display device and has a pointing device, such as a keyboard and/or a mouse, as the input device. The storage is, for example, a hard disk drive or a solid state drive (SSD). In addition, a computer may be provided with a graphics processing unit (GPU) if necessary.

A fluid analysis program according to this embodiment is installed in the computer. The computer executes the fluid analysis program to function as the fluid analysis apparatus 1. Further, the fluid analysis apparatus 1 has a function of requesting the medical image storage server 2 to transmit an image and a function of receiving an image from the medical image storage server 2 and executes a software program for each function to perform the functions.

The fluid analysis program is recorded on a recording medium, such as a digital versatile disc (DVD) or a compact disc read only memory (CD-ROM), and is then distributed. The fluid analysis program is read from the recording medium and is installed in the computer. Alternatively, the fluid analysis program may be stored in a storage device of a server computer connected to the network or a network storage such that it can be accessed from the outside, may be downloaded to the computer in response to a request from the outside, and may be installed.

Figure 2:
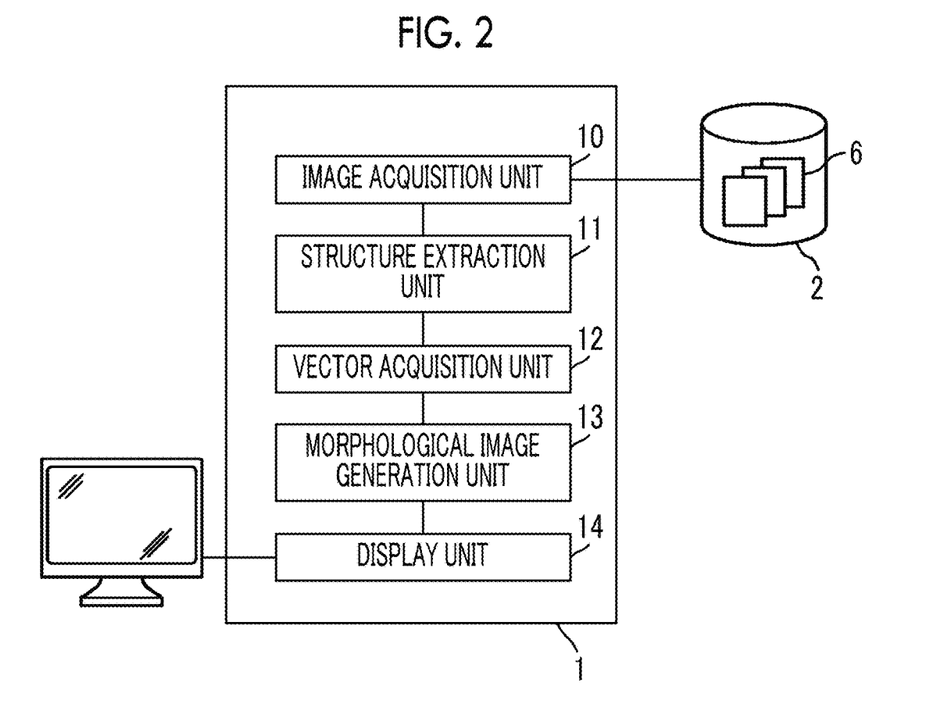
FIG. 2 is a diagram schematically illustrating the configuration of a fluid analysis apparatus according to a first embodiment of the invention.

As illustrated in FIG. 2, the fluid analysis apparatus 1 comprises an image acquisition unit 10, a structure extraction unit 11, a vector acquisition unit 12, a morphological image generation unit 13, and a display unit 14.

The image acquisition unit 10 acquires three-dimensional volume data 6 of a patient which has been captured in advance. In this embodiment, the three-dimensional volume data 6 is data captured by, for example, a CT apparatus, an MRI apparatus, or an ultrasonography apparatus.

The three-dimensional volume data 6 is stored in advance in the medical image storage server 2 together with the identification information of the patient. The image acquisition unit 10 reads one or more kinds of three-dimensional volume data 6 having the identification information of the patient from the medical image storage server 2 on the basis of the identification information of the patient input by the user through an input device, such as a keyboard, and stores the read three-dimensional volume data 6 in the storage (not illustrated). In addition, the three-dimensional volume data 6 is a CT image, a contrast-enhanced CT image, an MM image, a contrast-enhanced MM image, or volume data captured by a three-dimensional cine phase contrast magnetic resonance method (3D cine PC MRI). In this embodiment, a plurality of kinds of three-dimensional volume data obtained by capturing the image of the same part of the same patient are stored in the storage.

The structure extraction unit 11 extracts an anatomical structure from the three-dimensional volume data 6. Hereinafter, in this embodiment, a case in which the image acquisition unit 10 acquires the three-dimensional volume data 6 of the chest of the patient, the anatomical structure is a blood vessel, and the fluid is blood will be described. Hereinafter, the structure extraction unit 11 is described as a blood vessel region extraction unit 11.

The blood vessel region extraction unit 11 extracts a blood vessel region (a region of the anatomical structure) from the three-dimensional volume data 6. Specifically, the blood vessel region is extracted using a CT image (or a contrast-enhanced CT image) or an MRI image (or a contrast-enhanced MM image). A case in which the blood vessel region extraction unit 11 according to this embodiment extracts a blood vessel region from the CT image of the chest will be described. For example, the blood vessel region extraction unit 11 performs multi-resolution conversion for the three-dimensional volume data 6 of the chest to generate a plurality of images with different resolutions and performs eigenvalue analysis for the images with each resolution using a Hessian matrix to extract a line structure. In addition, the blood vessel region extraction unit 11 integrates the analysis results of the images with each resolution and extracts a blood vessel region as an aggregate of line structures with various sizes in a chest region (for example, see Y Sato, et al., "Three-dimensional multi-scale line filter for segmentation and visualization of curvilinear structures in medical images.", Medical Image Analysis, June 1998, Vol. 2, No. 2, p.p. 143-168). Furthermore, the blood vessel region extraction unit 11 connects center lines of the extracted line structures using, for example, a minimum spanning tree algorithm to generate tree structure data indicating a blood vessel. Alternatively, the blood vessel region extraction unit 11 may calculate cross sections orthogonal to a core line at each point on the core line connecting the center lines of the blood vessels, recognize the contour of the blood vessel in each cross section, and extract a blood vessel region on the basis of information indicating the contour, using a known segmentation method such as a graph cut method.

A method for extracting the blood vessel region is not limited to the above-mentioned method and other known methods, such as a region expansion method, may be used.

The vector acquisition unit 12 acquires a representative two-dimensional flow velocity vector representing a plurality of two-dimensional flow velocity vectors from two-dimensional flow velocity vectors obtained by projecting three-dimensional flow velocity vectors indicating the flow velocity and flow direction of blood in the blood vessel region onto a projection plane. The three-dimensional flow velocity vector can be acquired by various methods. For example, the image acquisition unit 10 acquires the three-dimensional volume data 6 captured by the three-dimensional cine phase contrast magnetic resonance method and the three-dimensional flow velocity vector is acquired using velocity information in the blood vessel region acquired on the basis of the three-dimensional volume data 6.

Next, a specific example of a case in which the representative two-dimensional flow velocity vector is acquired on the basis of volume data captured by the three-dimensional cine phase contrast magnetic resonance method using an MRI apparatus will be described.

Figure 3:
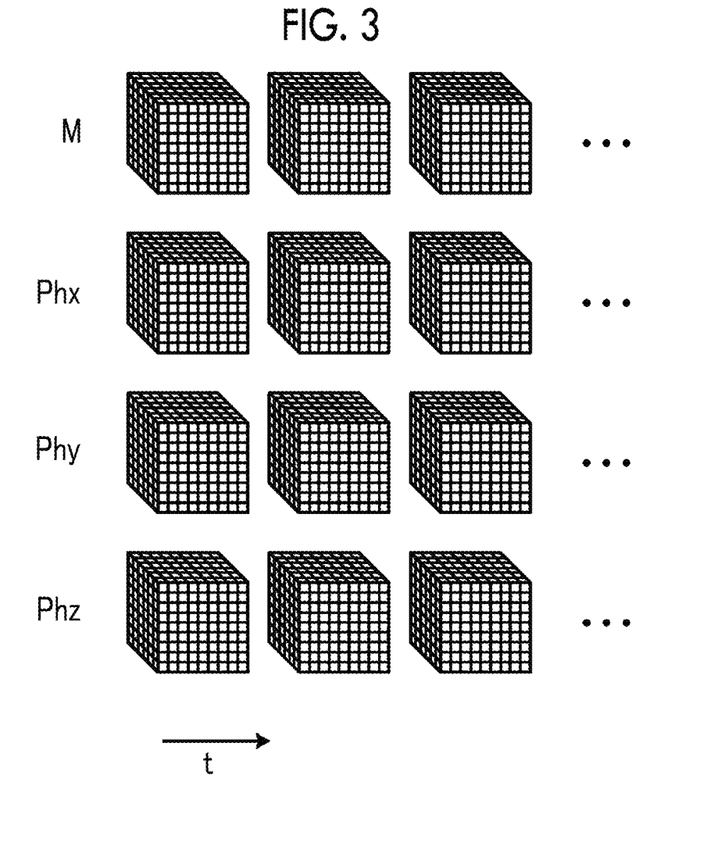
FIG. 3 is a diagram illustrating volume data captured by a three-dimensional cine phase contrast magnetic resonance method.

As illustrated in FIG. 3, the volume data captured by the three-dimensional cine phase contrast magnetic resonance method is volume data obtained by arranging magnitude data M and phase data Phx in the X-axis direction, phase data Phy in the Y-axis direction, and phase data Phz in the Z-axis direction subjected to encoding (velocity encoding (VENC)) in the X-axis direction, the Y-axis direction, and the Z-axis direction which are arranged in a predetermined cycle (for example, a cardiac cycle) along time t. The phase data Phx in the X-axis direction, the phase data Phy in the Y-axis direction, and the phase data Phz in the Z-axis direction indicate flow velocities in each axis direction. The three-dimensional flow velocity vector at each voxel position is obtained from three phase data items.

Figure 4:
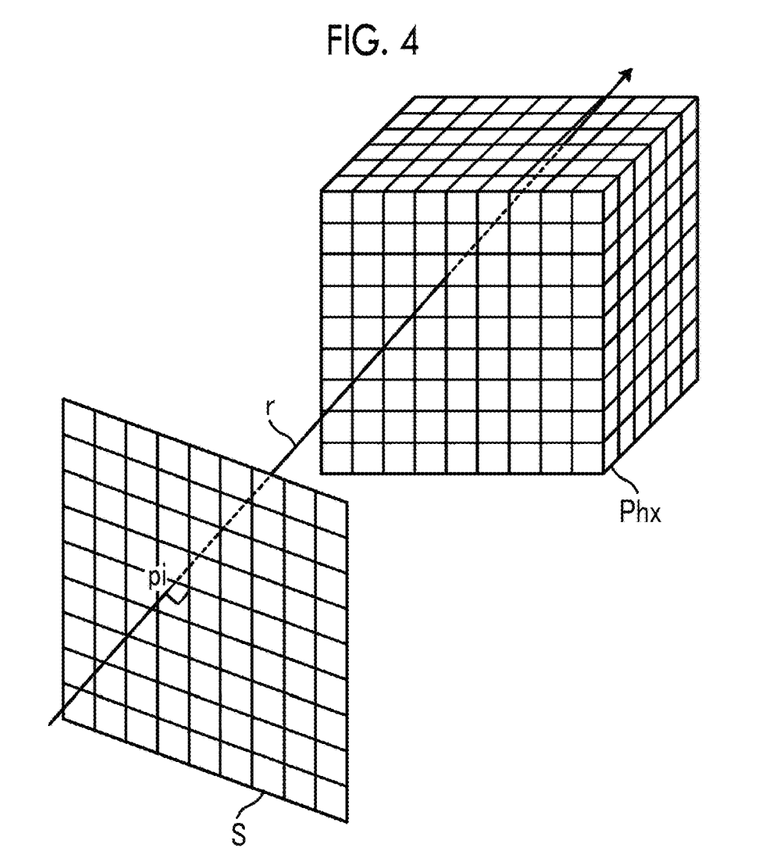
FIG. 4 is a diagram illustrating a method for acquiring a three-dimensional flow velocity vector.

As illustrated in FIG. 4, for each of the phase data Phx, the phase data Phy, and the phase data Phz, it is determined whether each voxel, through which a ray r that extends from one pixel pi in a projection plane in a direction perpendicular to the projection plane S (hereinafter, referred to as a projection direction) passes, is in the blood vessel region on the basis of the result of the blood vessel region extraction unit 11. In a case in which the voxel is in the blood vessel region, a velocity component in each axis direction is obtained from each voxel of each of the phase data Phx, the phase data Phy, and the phase data Phz and a three-dimensional flow velocity vector is sampled. FIG. 4 illustrates an example of the phase data Phx in the X-axis direction.

Similarly, for the phase data Phy in the Y-axis direction and the phase data Phz in the Z-axis direction, a velocity component is obtained from the voxel through which the ray r passes and velocity components in three directions are obtained. The CT image from which the blood vessel region has been extracted by the blood vessel region extraction unit 11 and each of the phase data Phx, the phase data Phy, and the phase data Phz captured by the three-dimensional cine phase contrast magnetic resonance method are aligned such that the same positions correspond to each other. The volume data items may be aligned with each other by a known method such as a method for aligning feature points of an imaging part.

Figure 5:
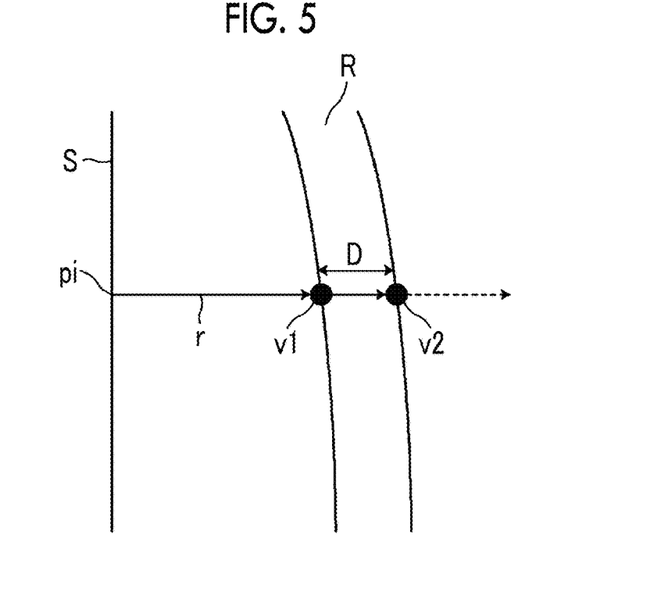
FIG. 5 is a diagram illustrating a method for acquiring a three-dimensional flow velocity vector in a blood vessel region.

As illustrated in FIG. 5, the ray r extends from the pixel pi in the projection plane S and the three-dimensional flow velocity vector of a voxel v1 entering a blood vessel region R is acquired. Further, the three-dimensional flow velocity vector of a voxel in a section D in which the ray r extends and comes out of the blood vessel region R is sampled. However, in a case in which all of a plurality of sampled three-dimensional flow velocity vectors are projected onto the projection plane S, vectors (arrows) overlap each other as illustrated on the left side of FIG. 6. As a result, an image is difficult to see. For this reason, only one representative two-dimensional flow velocity vector is calculated from a plurality of sampled three-dimensional flow velocity vectors for each pixel. Therefore, it is possible to reduce the number of two-dimensional flow velocity vectors to be displayed as illustrated on the right side of FIG. 6.

Figure 6:
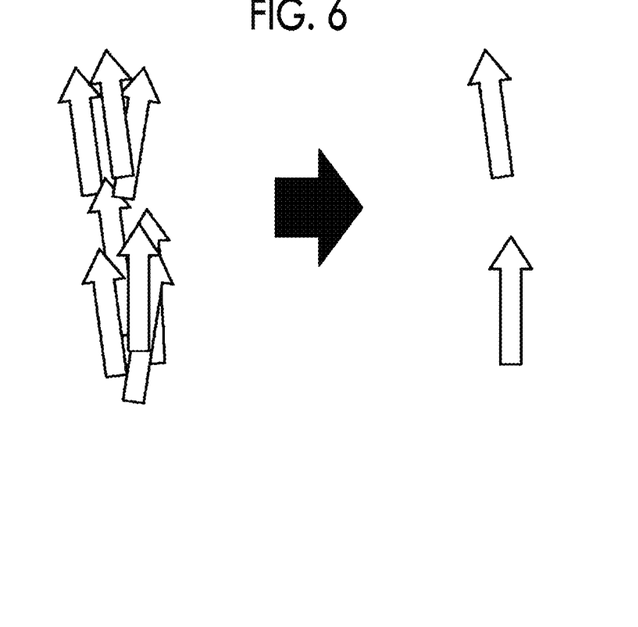
FIG. 6 is a diagram illustrating a method for acquiring a representative two-dimensional flow velocity vector.

For example, a two-dimensional flow velocity vector obtained by projecting a three-dimensional flow velocity vector with the maximum size among the three-dimensional flow velocity vectors that overlap each other in the projection direction, that is, the voxels of the blood vessel region R through which the ray r passes is used as the representative two-dimensional flow velocity vector. Alternatively, a two-dimensional flow velocity vector obtained by projecting an average three-dimensional flow velocity vector obtained by averaging the three-dimensional flow velocity vectors of the voxels of the blood vessel region R through which the ray r passes is used as the representative two-dimensional flow velocity vector.

Alternatively, a two-dimensional flow velocity vector with the maximum size among the two-dimensional flow velocity vectors obtained by projecting the three-dimensional flow velocity vectors of the voxels of the blood vessel region R through which the ray r passes may be used as the representative two-dimensional flow velocity vector. In addition, an average two-dimensional flow velocity vector obtained by averaging the two-dimensional flow velocity vectors obtained by projecting the three-dimensional flow velocity vectors of the voxels of the blood vessel region R through which the ray r passes may be used as the representative two-dimensional flow velocity vector.

However, in a case in which all of the voxels of the blood vessel region are sampled and two or more blood vessels overlap each other in the projection direction, the flow velocity vectors of not only the blood vessel in front of the projection plane but also the blood vessel behind on the projection plane are displayed. For example, a vector that traverses the blood vessel is displayed in the vicinity of the center of FIG. 14. As such, since the flow velocity vector of the blood vessel on the rear side is displayed, it is difficult to intuitively check the tendency of a blood flow. In addition, in a case in which the vein and the artery overlap each other, there is a difference in the magnitude of the flow velocity. Therefore, it is difficult to accurately check a blood flow in a case in which all of the three-dimensional flow velocity vectors of the blood vessels that overlap each other are displayed.

Figure 7:
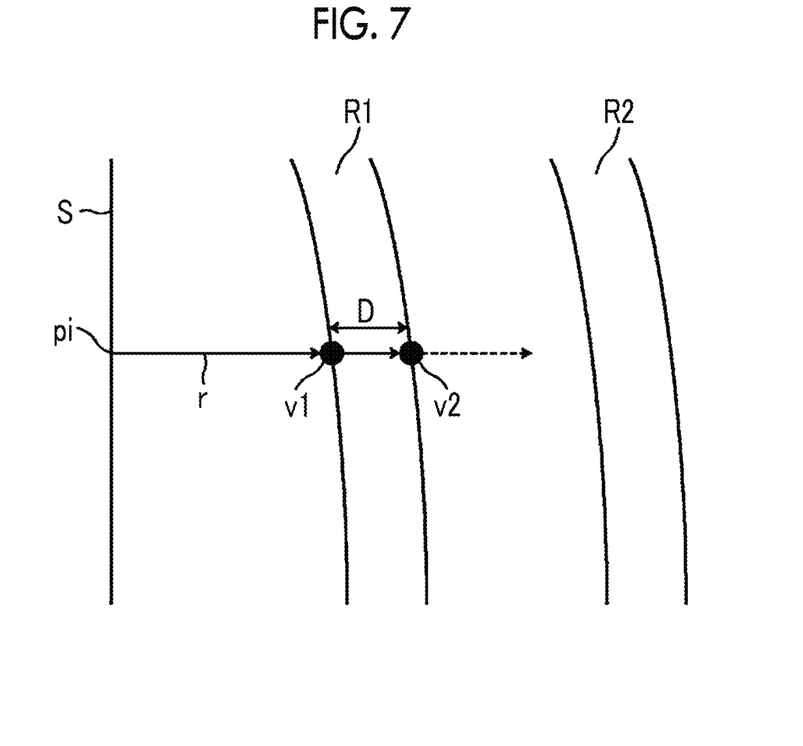
FIG. 7 is a diagram illustrating a method for acquiring a three-dimensional flow velocity vector from a blood vessel region close to a projection plane among blood vessels that overlap each other in a projection direction.

As illustrated in FIG. 7, in a case in which the blood vessels overlap each other in the projection direction and are separated from each other, the three-dimensional flow velocity vector is sampled only from a position v1 where the ray r enters the blood vessel region R1 and extends to a position v2 where the ray r comes out of the blood vessel region R1. In this case, only the three-dimensional flow velocity vector in the blood vessel region R1 close to the projection plane S can be sampled and the three-dimensional flow velocity vector in a blood vessel region R2 on the rear side which is far from the projection plane S is not sampled.

The case in which the three-dimensional flow velocity vector is acquired from the volume data captured by the three-dimensional cine phase contrast magnetic resonance method has been described above. Blood flow analysis using computational fluid dynamics (CFD) may be performed using the blood vessel region extracted by the blood vessel region extraction unit 11 to acquire the flow velocity vector. For example, blood flow analysis can be performed using blood vessel regions extracted from each of the CT images captured in time series. Specifically, a contrast-enhanced CT image or a contrast-enhanced MRI image can be used.

The image acquisition unit 10 may acquire a three-dimensional ultrasound image captured in time series by Doppler measurement and a flow velocity vector may be acquired using velocity information in the blood vessel region acquired on the basis of the ultrasound image.

The morphological image generation unit 13 performs a volume rendering process for a CT image or an MM image to generate a morphological image. In a case in which a morphological image is generated, particularly, it is desirable to generate a morphological image, using an image in which a blood vessel region and other regions are clearly distinguished from each other, such as a contrast-enhanced CT image or a contrast-enhanced MRI image.

The display unit 14 displays the representative two-dimensional flow velocity vector acquired by the vector acquisition unit 12 on a display so as to be superimposed on the morphological image generated by the morphological image generation unit 13.

The size of the displayed representative two-dimensional flow velocity vector becomes small in a case in which blood flows in the depth direction and becomes large in a case in which blood flows in a direction parallel to the projection plane. Therefore, the display of the representative two-dimensional flow velocity vector projected to the projection plane makes it possible to estimate the direction in which blood flows.

Figure 8:
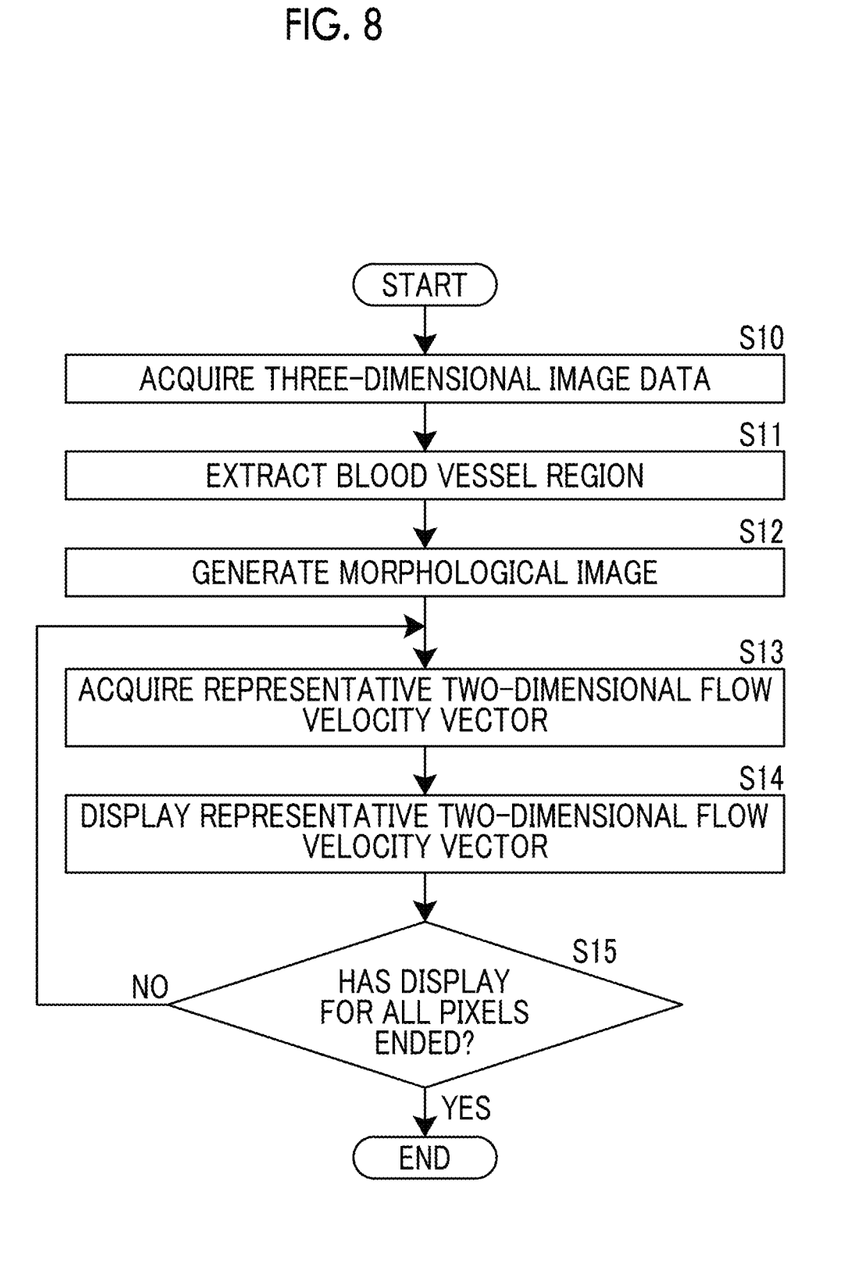
FIG. 8 is a flowchart illustrating the flow of a process of the fluid analysis apparatus.

Next, the flow of the process of the fluid analysis apparatus 1 according to the first embodiment will be described with reference to a flowchart illustrated in FIG. 8.

First, the image acquisition unit 10 acquires a contrast-enhanced CT image of a patient and volume data captured by the three-dimensional cine phase contrast magnetic resonance method in response to, for example, the input of settings, such as the identification information of the patient, by the user (S10).

Then, the blood vessel region extraction unit 11 extracts a blood vessel region using the contrast-enhanced CT image of the chest acquired by the image acquisition unit 10 (S11). In addition, the morphological image generation unit 13 generates a morphological image (S12).

The display unit 14 displays the morphological image of the blood vessel generated by the morphological image generation unit 13. The vector acquisition unit 12 scans the pixels on the projection plane S to acquire a representative two-dimensional flow velocity vector at each pixel position. First, the vector acquisition unit 12 emits the ray r from a first pixel on the projection plane S, acquires the three-dimensional flow velocity vectors of voxels corresponding to the blood vessel region extracted by the blood vessel region extraction unit 11 among the voxels through which the ray r passes in the volume data captured by the three-dimensional cine phase contrast magnetic resonance method, and acquires a representative two-dimensional flow velocity vector of the two-dimensional flow velocity vectors obtained by projecting the three-dimensional flow velocity vectors onto the projection plane S (S13).

The display unit 14 displays an arrow indicating the representative two-dimensional flow velocity vector acquired by the vector acquisition unit 12 on the display so as to be superimposed on the morphological image of the blood vessel (S14). Then, the vector acquisition unit 12 emits the ray r from a second pixel, acquires a representative two-dimensional flow velocity vector from the three-dimensional flow velocity vectors of voxels corresponding to the blood vessel region extracted by the blood vessel region extraction unit 11 among the voxels through which the ray r passes in each phase data item of the volume data captured by the three-dimensional cine phase contrast magnetic resonance method (S13), and displays an arrow indicating the acquired representative two-dimensional flow velocity vector on the display so as to be superimposed on the morphological image of the blood vessel (S14). As described above, the process in S13 and S14 is repeated until the process for all of the pixels of the projection plane S ends (S15—NO). In a case in which the process in S13 and S14 for all of the pixels ends, the process of the fluid analysis apparatus ends (S15—YES).

Figure 9:
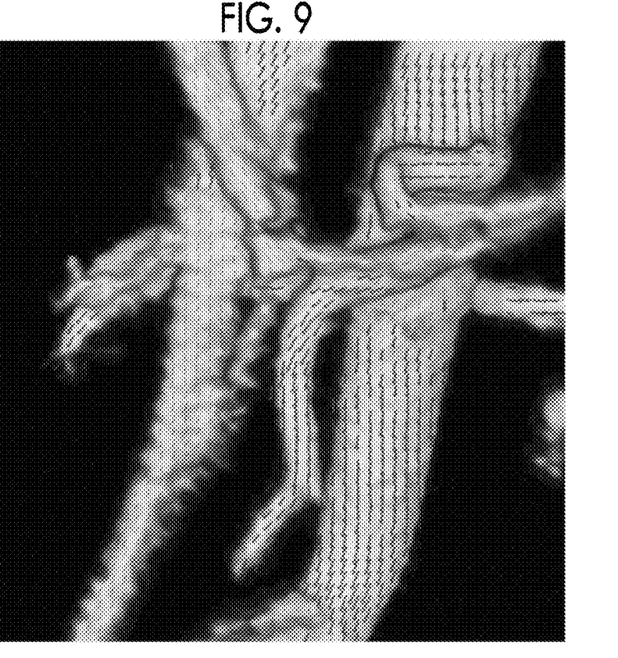
FIG. 9 illustrates an example in which the representative two-dimensional flow velocity vector is displayed so as to be superimposed on a morphological image.

FIG. 9 illustrates an example of the case in which the representative two-dimensional flow velocity vector is displayed so as to be superimposed on the morphological image. Since only one arrow is displayed in one pixel, it is easy to understand the flow of blood. As such, the fluid analysis apparatus 1 makes it easy to check the flow of blood. Therefore, it is possible to observe a portion in which blood flows backward in the artery coming out of the heart or a portion in which blood flows in a spiral shape in the aneurysm, which makes it easy to perform a diagnosis.

In the first embodiment, the case in which a blood flow is analyzed has been described. However, the anatomical structure may be a region in which cerebrospinal fluid flows, such as the brain, and the fluid may be cerebrospinal fluid. In a case in which the anatomical structure is the brain, the morphological image generation unit 13 generates a morphological image obtained by performing volume rendering for the brain. The representative two-dimensional flow velocity vector is displayed so as to be superimposed on the generated morphological image.

Next, a fluid analysis apparatus according to a second embodiment of the invention will be described. This embodiment differs from the fluid analysis apparatus according to the first embodiment in a method for determining a blood vessel region close to the projection plane in a case in which the blood vessels overlap each other in the projection direction. In this embodiment, only configurations different from those in the first embodiment will be described and the description of the same configurations as those in the first embodiment will not be described. In this embodiment, similarly to the first embodiment, a case in which the anatomical structure is a blood vessel and the fluid is blood will be described.

In the first embodiment, the case in which a plurality of blood vessels overlap each other in the projection direction and the overlapped blood vessels are separated from each other has been described. However, in a case in which a plurality of blood vessels overlap each other in the projection direction and the blood vessel regions of the blood vessels are adjacent to each other, it is difficult to detect the boundary between the blood vessel regions in the method according to the first embodiment. Therefore, in some cases, it is difficult to extract only the blood vessel region close to the projection plane. For this reason, in this embodiment, a method which can acquire a three-dimensional flow velocity vector only in the blood vessel region close to the projection plane even in a case in which the blood vessel regions of the blood vessels overlapping in the projection direction are adjacent to each other will be described with reference to the drawings. The same configurations as those in the first embodiment are denoted by the same reference numerals and the detailed description thereof will not be repeated.

Figure 10:
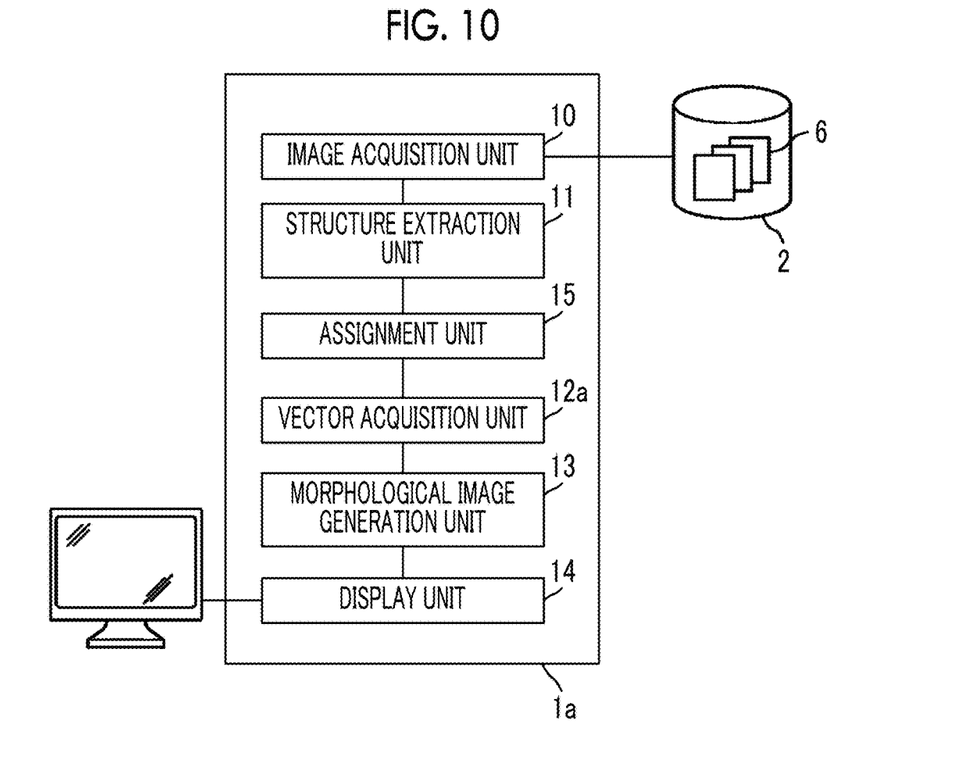
FIG. 10 is a diagram schematically illustrating the configuration of a fluid analysis apparatus according to a second embodiment of the invention.

As illustrated in FIG. 10, a fluid analysis apparatus 1a according to this embodiment comprises an image acquisition unit 10, a structure extraction unit 11, a vector acquisition unit 12a, a morphological image generation unit 13, a display unit 14, and an assignment unit 15. The structure extraction unit 11 will be described below as a blood vessel region extraction unit 11 as in the first embodiment.

The assignment unit 15 assigns route position information that can identify the order of positions along a blood vessel route to each position in the blood vessel.

Figure 11:
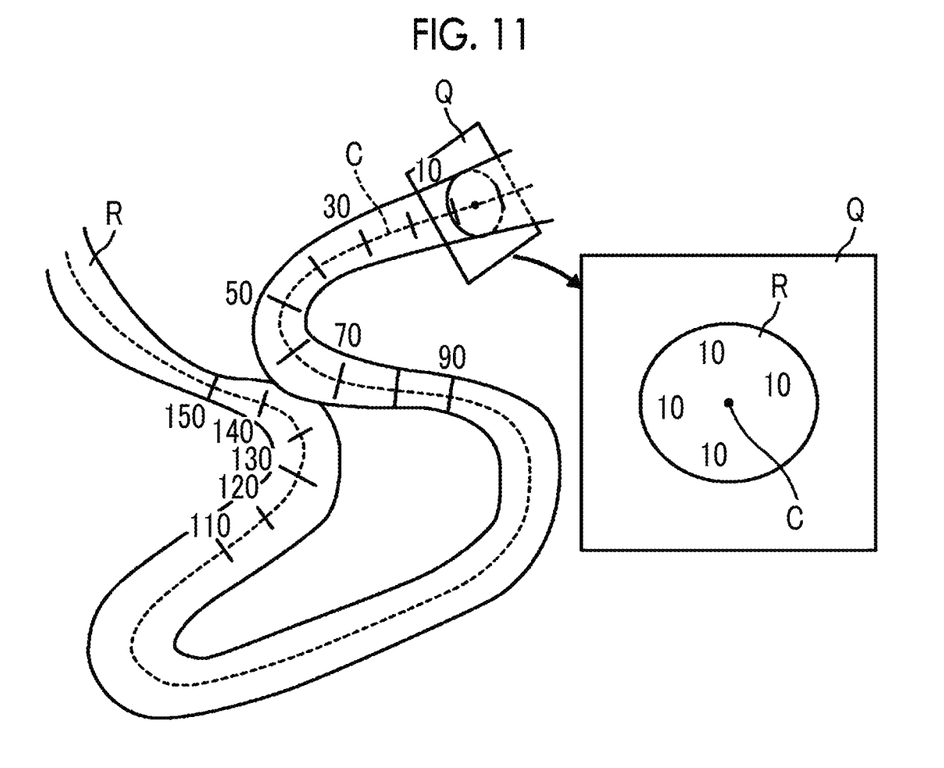
FIG. 11 is a diagram illustrating a method for assigning route position information.

First, as illustrated in FIG. 11, a center line C of the blood vessel region extracted by the blood vessel region extraction unit 11 is extracted. The assignment unit 15 sequentially assigns the route position information that is uniquely determined to each voxel of the center line C along the route. Specifically, as the route position information, consecutive numbers are sequentially assigned from a predetermined point on the center line. For example, as the route position information, numbers are assigned in the order of 1, 2, 3, . . . along the route. FIG. 11 illustrates an example in which numbers are assigned in increments of 10. A vertical cross section Q is set at each position of the center line C of the blood vessel region R and the same route position information as the route position information of the center line C is assigned to all of the voxels in the blood vessel region R. As illustrated in an enlarged view on the right side of FIG. 11, in a case in which the route position information of the voxel corresponding to the center line C is "10", all of the route position information items of the voxels in the blood vessel region R included in the vertical cross section Q are "10".

Figure 12:
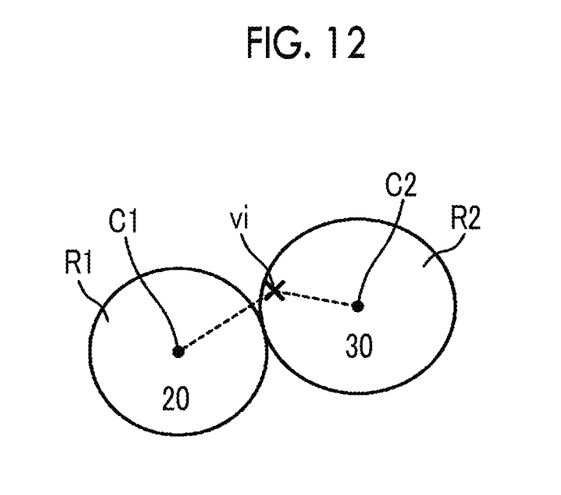
FIG. 12 is a diagram illustrating a method for assigning route position information in a place where two blood vessel regions are adjacent to each other.

As illustrated in FIG. 12, in a place where two blood vessel regions R1 and R2 are adjacent to each other, the route position information of a blood vessel region having the shorter distance from each voxel vi to the center lines C1 and C2 of the two blood vessel regions R1 and R2 is assigned to the voxels of the blood vessel region. FIG. 12 illustrates a case in which the route position information of the voxel in the vertical cross section of the center line C1 is "20" and the route position information of the voxel in the vertical cross section of the center line C2 is "30". Of the distance from the voxel vi to the center line C1 and the distance from the voxel vi to the center line C2, the distance from the voxel vi to the center line C2 is short. Therefore, the route position information of the voxel vi is "30".

Figure 13:
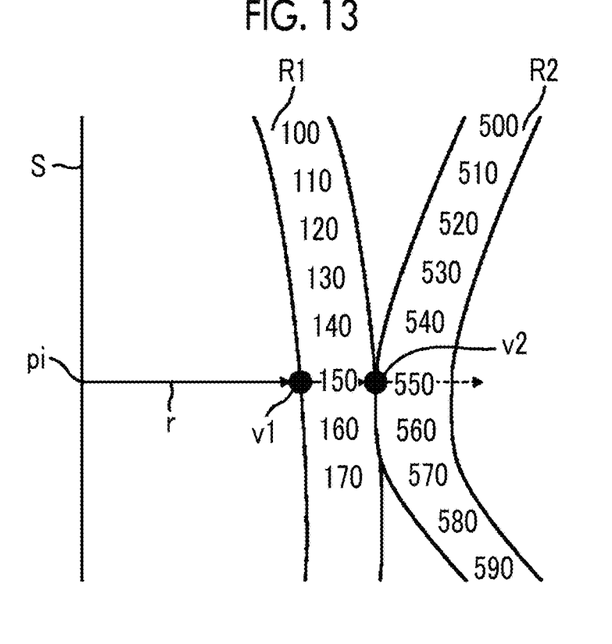
FIG. 13 is a diagram illustrating a method for acquiring a three-dimensional flow velocity vector from a blood vessel region close to the projection plane among blood vessels that overlap each other in the projection direction.

As illustrated in FIG. 13, in a case in which the blood vessels overlap each other in the projection direction and are adjacent to each other, the vector acquisition unit 12a samples the three-dimensional flow velocity vector only in a section from the voxel v1 at the position where the ray r enters the blood vessel region R1 to the voxel v2 at the position where the ray r comes out of the blood vessel region R1. In this case, sampling is performed up to the place where the route position information of each voxel assigned by the assignment unit 15 does not change significantly. The three-dimensional flow velocity vector from the voxel v1 to the voxel v2 is sampled. In FIG. 13, the route position information of the voxel v1 is "150" and the route position information of the voxel v2 is "550". Since the route position information is significantly different from "150", it is determined that the ray R has entered another blood vessel region R2. The representative two-dimensional flow velocity vector is calculated from the three-dimensional flow velocity vector of the voxel to which route position information "150" is assigned. A method for calculating the representative two-dimensional flow velocity vector from the three-dimensional flow velocity vector is the same as that in the first embodiment.

FIG. 13 illustrates an example of the case in which all of the route position information items from the voxel v1 to the voxel v2 are "150". However, in some cases, the route position information items from the voxel v1 to the voxel v2 are numbers before and after "150", for example, numbers close to "150", such as "149" or "151", depending on the travel direction of the blood vessel and the direction of the ray r. In a case in which the route position information is a number within a predetermined range and it is determined that the route position information items of adjacent voxels are within the same blood vessel region R1 from the size of the voxel and the width of the blood vessel, it is determined that, of the blood vessel regions R1 and R2 overlapping each other, the blood vessel region R1 is close to the projection plane S. As such, in a case in which adjacent voxels have different route position information items and are determined not to be in the same blood vessel region R1, it is determined that the ray r has passed the blood vessel wall and entered the next blood vessel region R2.

The case in which one computer functions as the fluid analysis apparatus has been described above. However, the functions of the fluid analysis apparatus may be dispersed to a plurality of computers. For example, another computer only for image processing may extract an anatomical structure and/or generate a morphological image and a computer that displays the result of the fluid analysis process may receive the information of the anatomical structure and/or the morphological image from the computer only for image processing, display the morphological image, and display the representative two-dimensional flow velocity vector so as to be superimposed on the morphological image.

The case in which a general-purpose computer functions as the fluid analysis apparatus has been described above. However, a dedicated computer may function as the fluid analysis apparatus. The dedicated computer may be firmware that executes a program recorded on a non-volatile memory, such as a built-in read only memory (ROM) or a flash memory. Furthermore, a dedicated circuit, such as an application specific integrated circuit (ASIC) or a field programmable gate array (FPGA) that permanently stores a program for implementing at least some of the functions of the fluid analysis apparatus, may be provided. Alternatively, program commands that are stored in a dedicated circuit may be combined with program commands which are executed by a general-purpose CPU programmed to use a program of the dedicated circuit. As described above, program commands may be executed by any combination of the hardware configurations of the computers.

EXPLANATION OF REFERENCES 1, 1a: fluid analysis apparatus
2: medical image storage server
3: imaging apparatus
4: network
6: three-dimensional volume data
10: image acquisition unit
11: structure extraction unit
12, 12a: vector acquisition unit
13: morphological image generation unit
14: display unit
15: assignment unit

What is claimed is:

1. A fluid analysis apparatus comprising:
a display panel; and
a processor coupled to the display panel and configured to:
acquire, from three-dimensional volume data obtained by capturing an image of an object including an anatomical structure in which a fluid flows, information of a plurality of three-dimensional flow velocity vectors which are projected to a projection plane and indicates a flow velocity of the fluid in the anatomical structure for each voxel,
acquire, from the plurality of three-dimensional flow velocity vectors, a representative two-dimensional flow velocity vector representing overlapping three-dimensional flow velocity vectors of a plurality of two-dimensional flow velocity vectors obtained by projecting three-dimensional flow velocity vectors that overlap each other in the projection direction respectively, wherein, wherein the projection direction is at least substantially perpendicular to the projection plane, the representative two-dimensional flow velocity vector is a two-dimensional flow velocity vector with a maximum size among the plurality of two-dimensional flow velocity vectors obtained by projecting the three-dimensional flow velocity vectors that overlap each other in the projection direction; and
control the display panel to display, in a case where at least two blood vessel regions do not overlap with each other, two-dimensional flow velocity vectors obtained by projecting three-dimensional flow velocity vectors that do not overlap each other in the projection direction to the projection plane and the representative two-dimensional flow velocity vector projected to the projection plane by displaying the representative two-dimensional flow velocity vector with the maximum size in place of the three-dimensional flow velocity vectors that overlap each other in the projection direction.

2. The fluid analysis apparatus according to claim 1,
wherein the object includes a plurality of anatomical structures, and
wherein, in a case in which the anatomical structures at least partially overlap each other in the projection direction, the representative two-dimensional flow velocity vector is a two-dimensional flow velocity vector representing two-dimensional flow velocity vectors obtained by respectively projecting three-dimensional flow velocity vectors in an anatomical structure close to the projection plane among the anatomical structures having the overlapped portion.

3. The fluid analysis apparatus according to claim 1,
wherein the plurality of three-dimensional flow velocity vectors are acquired from three-dimensional volume data captured by a three-dimensional cine phase contrast magnetic resonance method.

4. The fluid analysis apparatus according to claim 2,
wherein the plurality of three-dimensional flow velocity vectors are acquired from three-dimensional volume data captured by a three-dimensional cine phase contrast magnetic resonance method.

5. The fluid analysis apparatus according to claim 1,
wherein the display unit displays the representative two-dimensional flow velocity vector so as to be superimposed on a morphological image of the anatomical structure.

6. The fluid analysis apparatus according to claim 2,
wherein the display unit displays the representative two-dimensional flow velocity vector so as to be superimposed on a morphological image of the anatomical structure.

7. The fluid analysis apparatus according to claim 1,
wherein the anatomical structure is a blood vessel, the fluid is blood, and the plurality of three-dimensional flow velocity vectors are flow velocity vectors of the blood.

8. The fluid analysis apparatus according to claim 7,
wherein the plurality of three-dimensional flow velocity vectors are obtained by a result of blood flow analysis using computational fluid dynamics.

9. The fluid analysis apparatus according to claim 1,
wherein the fluid is cerebrospinal fluid and the plurality of three-dimensional flow velocity vectors are flow velocity vectors of the cerebrospinal fluid.

10. A method for operating the fluid analysis apparatus according to claim 1 comprising the processor and the display unit, the method comprising:
configuring the processor to acquire, from the three-dimensional volume data obtained by capturing the image of the object including the anatomical structure in which the fluid flows, the information of the plurality of three-dimensional flow velocity vectors indicating the flow velocity of the fluid in the anatomical structure for each voxel, and to acquire, from the plurality of two-dimensional flow velocity vectors obtained by projecting the three-dimensional flow velocity vectors of the plurality of voxels overlapping in the projection direction of the projection plane to the projection plane, the representative two-dimensional flow velocity vector representing the plurality of two-dimensional flow velocity vectors obtained by projecting the three-dimensional flow velocity vectors that overlap each other in the projection direction respectively, wherein the representative two-dimensional flow velocity vector is a two-dimensional flow velocity vector with a maximum size among two-dimensional flow velocity vectors obtained by projecting the three-dimensional flow velocity vectors that overlap each other in the projection direction or an average two-dimensional flow velocity vector obtained by averaging the two-dimensional flow velocity vectors obtained by projecting the three-dimensional flow velocity vectors that overlap each other in the projection direction; and
allowing the display unit to display the representative two-dimensional flow velocity vector projected to the projection plane by displaying the representative two-dimensional flow velocity vector with the maximum size in place of the three-dimensional flow velocity vectors that overlap each other in the projection direction or by displaying the average two-dimensional flow velocity vector in place of the three-dimensional flow velocity vectors that overlap each other in the projection direction in a case where at least two blood vessel regions do not overlap with each other.

11. A non-transitory computer readable recording medium storing a fluid analysis program that causes a computer to function as the fluid analysis apparatus according to claim 1, the function comprising:
   causing the processor to acquire, from the three-dimensional volume data obtained by capturing the image of the object including the anatomical structure in which the fluid flows, the information of the plurality of three-dimensional flow velocity vectors indicating the flow velocity of the fluid in the anatomical structure for each voxel, and to acquire, from the plurality of two-dimensional flow velocity vectors obtained by projecting the three-dimensional flow velocity vectors of the plurality of voxels overlapping in the projection direction of the projection plane to the projection plane, the representative two-dimensional flow velocity vector representing the plurality of two-dimensional flow velocity vectors obtained by projecting the three-dimensional flow velocity vectors that overlap each other in the projection direction respectively, wherein the representative two-dimensional flow velocity vector is a two-dimensional flow velocity vector with a maximum size among two-dimensional flow velocity vectors obtained by projecting the three-dimensional flow velocity vectors that overlap each other in the projection direction or an average two-dimensional flow velocity vector obtained by averaging the two-dimensional flow velocity vectors obtained by projecting the three-dimensional flow velocity vectors that overlap each other in the projection direction; and
   causing the display unit to display the representative two-dimensional flow velocity vector projected to the projection plane by displaying the representative two-dimensional flow velocity vector with the maximum size in place of the three-dimensional flow velocity vectors that overlap each other in the projection direction or by displaying the average two-dimensional flow velocity vector in place of the three-dimensional flow velocity vectors that overlap each other in the projection direction in a case where at least two blood vessel regions do not overlap with each other.

12. The fluid analysis apparatus according to claim 1, wherein the processor is further configured to only display a plurality of two-dimensional flow velocity vectors obtained by projecting three-dimensional flow velocity vectors to the projection plane from a blood vessel region of the at least two blood vessel regions that is closest to the projection plane in a case where the anatomical structure includes at least two blood vessels overlapping with each other in a direction orthogonal to the projection plane but are not physically touching each other.

13. The fluid analysis apparatus according to claim 1, wherein the processor is further configured to only display a plurality of two-dimensional flow velocity vectors obtained by projecting three-dimensional flow velocity vectors to the projection plane from a blood vessel region of the at least two blood vessel regions that is closest to the projection plane and has a same route position information as in a case where the anatomical structure includes at least two blood vessels overlapping with each other in a direction orthogonal to the projection plane and are physically touching each other.

14. A fluid analysis apparatus comprising:
   a display panel; and
   a processor coupled to the display panel and configured to:
      acquire, from three-dimensional volume data obtained by capturing an image of an object including an anatomical structure in which a fluid flows, information of a plurality of three-dimensional flow velocity vectors which are projected to a projection plane and indicates a flow velocity of the fluid in the anatomical structure for each voxel,
      acquire, from the plurality of three-dimensional flow velocity vectors, a representative two-dimensional flow velocity vector is representing overlapping three-dimensional flow velocity vectors of a plurality of two-dimensional flow velocity vectors by projecting three-dimensional flow velocity vectors that overlap each other in the projection direction respectively, wherein the projection direction is at least substantially perpendicular to the projection plane, the representative two-dimensional flow velocity vector is a two-dimensional flow velocity vector with an average of the plurality of two-dimensional flow velocity vectors obtained by projecting the three-dimensional flow velocity vectors that overlap each other in the projection direction; and
      control the display panel to display, in a case where at least two blood vessel regions do not overlap with each other, two-dimensional flow velocity vectors obtained by projecting three-dimensional flow velocity vectors that do not overlap each other in the projection direction to the projection plane and the representative two-dimensional flow velocity vector projected to the projection plane by displaying the average of the two-dimensional flow velocity vectors in place of the three-dimensional flow velocity vectors that overlap each other in the projection direction as the representative two-dimensional flow velocity vector.

15. The fluid analysis apparatus according to claim 14, wherein the plurality of three-dimensional flow velocity vectors are acquired from three-dimensional volume data captured by a three-dimensional cine phase contrast magnetic resonance method.

16. A fluid analysis apparatus comprising:
   a memory that stores commands to be executed by a computer; and
   a processor that is configured to execute the stored commands to perform
   a process of acquiring, from three-dimensional volume data that is obtained by capturing an image of an object including an anatomical structure in which a fluid flows and has information of a plurality of three-dimensional flow velocity vectors which are projected to a projection plane and indicates a flow velocity of the fluid in the anatomical structure for each voxel, acquiring, from the plurality of three-dimensional flow velocity vectors, a representative two-dimensional flow velocity vector representing overlapping three-dimensional flow velocity vectors of a plurality of two-dimensional flow velocity vectors obtained by projecting three-dimensional flow velocity vectors that overlap each other in a projection direction of a projection plane respectively, wherein, the projection direction is at least substantially perpendicular to the projection plane, the representative two-dimensional flow velocity vector is a two-dimensional flow velocity vector with a maximum size among the plurality of two-dimensional flow velocity vectors obtained by projecting the three-dimensional flow velocity vectors that overlap each other in the projection direction or an average two-dimensional flow velocity vector obtained by averaging the two-dimensional flow velocity vectors obtained by projecting the three-dimensional flow velocity vectors that overlap each other in the projection direction, and a process of displaying the representative two-dimensional flow velocity vector projected to the projection plane by displaying two-dimensional flow velocity vectors obtained by projecting three-dimensional flow velocity vectors that do not overlap each other in the projection direction to the projection plane and the representative two-dimensional flow velocity vector with the maximum size in place of the three-dimensional flow velocity vectors that overlap each other in the projection direction or by displaying the average two-dimensional flow velocity vector in place of the three-dimensional flow velocity vectors that overlap each other in the projection direction in a case where at least two blood vessel regions do not overlap with each other.

* * * * *